US011111571B2

(12) United States Patent
Cai et al.

(10) Patent No.: US 11,111,571 B2
(45) Date of Patent: Sep. 7, 2021

(54) NI-FREE BETA TI ALLOYS WITH SHAPE MEMORY AND SUPER-ELASTIC PROPERTIES

(71) Applicant: Fort Wayne Metals Research Products Corp, Fort Wayne, IN (US)

(72) Inventors: Song Cai, Fort Wayne, IN (US); Jeremy E. Schaffer, Fort Wayne, IN (US); Adam J. Griebel, Fort Wayne, IN (US)

(73) Assignee: Fort Wayne Metals Research Products, Fort Wayne, IN (US)

( * ) Notice: Subject to any disclaimer, the term of this patent is extended or adjusted under 35 U.S.C. 154(b) by 87 days.

(21) Appl. No.: 16/349,498

(22) PCT Filed: Nov. 14, 2016

(86) PCT No.: PCT/US2016/061843
§ 371 (c)(1),
(2) Date: May 13, 2019

(87) PCT Pub. No.: WO2018/089028
PCT Pub. Date: May 17, 2018

(65) Prior Publication Data
US 2019/0292640 A1  Sep. 26, 2019

(51) Int. Cl.
*C22C 14/00* (2006.01)
*C22F 1/00* (2006.01)
(Continued)

(52) U.S. Cl.
CPC ............ *C22F 1/006* (2013.01); *A61L 31/022* (2013.01); *A61L 31/14* (2013.01); *C22C 14/00* (2013.01);
(Continued)

(58) Field of Classification Search
CPC ............ C22C 14/00; C22F 1/183; C22F 1/006
See application file for complete search history.

(56) References Cited

U.S. PATENT DOCUMENTS

| 5,758,420 A | 6/1998 | Schmidt et al. |
| 6,527,802 B1 * | 3/2003 | Mayer .................... A61F 2/86 |
| | | 623/1.1 |

(Continued)

FOREIGN PATENT DOCUMENTS

| CN | 104245975 A | 12/2014 |
| JP | 2009-097064 | 5/2009 |
| WO | 2014182691 | 11/2014 |

OTHER PUBLICATIONS

International Preliminary Report on Patentability received for PCT Patent Application No. PCT/US2016/061843, dated Jul. 24, 2019, 10 pages.
(Continued)

*Primary Examiner* — Jessee R Roe
(74) *Attorney, Agent, or Firm* — Faegre Drinker Biddle & Reath LLP

(57) ABSTRACT

A group of substantially nickel-free beta-titanium alloys have shape memory and super-elastic properties suitable for, e.g., medical device applications. In particular, the present disclosure provides a titanium-based group of alloys including 16-20 at. % of hafnium, zirconium or a mixture thereof, 8-17 at. % niobium, and 0.25-6 at. % tin. This alloy group exhibits recoverable strains of at least 3.5% after axial, bending or torsional deformation. In some instances, the alloys have a capability to recover of more than 5% deformation strain. Niobium and tin are provided in the alloy to control beta phase stability, which enhances the ability of the materials to exhibit shape memory or super-elastic properties at a desired application temperature (e.g., body temperature). Hafnium and/or zirconium may be interchange- (Continued)

ably added to increase the radiopacity of the material, and also contribute to the superelasticity of the material.

32 Claims, 10 Drawing Sheets

(51) Int. Cl.
*A61L 31/02* (2006.01)
*C22F 1/18* (2006.01)
*A61L 31/14* (2006.01)
*C22C 27/00* (2006.01)

(52) U.S. Cl.
CPC .............. *C22C 27/00* (2013.01); *C22F 1/18* (2013.01); *C22F 1/183* (2013.01); *A61L 2400/16* (2013.01)

(56) References Cited

U.S. PATENT DOCUMENTS

| | | |
|---|---|---|
| 2009/0097064 A1 | 4/2009 | Tominaga |
| 2013/0139933 A1 | 6/2013 | Ju et al. |
| 2014/0338795 A1 | 11/2014 | Gloriant et al. |
| 2016/0151610 A1 | 6/2016 | Schaffer |

OTHER PUBLICATIONS

Elahinia et al.—Manufacturing and processing of NiTi inplants: A review. Progress in Materials Science 57 (2012) 911-946.
European Office Action dated Jan. 12, 2020 in corresponding European Patent Application No. 16921269.3. 9 pages.
Japanese Office Action dated Nov. 10, 2020 in corresponding Japanese Patent Application No. 2019-524054, 4 pages.
Chinese Office Action dated Nov. 6, 2020 in corresponding Japanese Patent Application No. 201680091540.2, 11 pages.
Hao, YL et al., Effect of Zr and Sn on Young's modulus and superelasticity of Ti—Nb based alloys, Materials Science and Engineering, vol. 441, No. 1, pp. 112-118; Dec. 15, 2006.
International Search Report and Written Opinion dated Jan. 23, 2017 in International Application No. PCT/US16/61843.
Brazilian Search Report dated Mar. 17, 2020 in corresponding Brazilian Patent Application No. BR112019009699-0.
European Search Report dated Feb. 13, 2020 in corresponding European Patent Application No. 16921269.3. 12 pages.
Jie Fu et al.—Novel Ti-base superelastic alloys with large recovery strain and excellent biocompatibility. Acta Biomaterialia 17 (2015) pp. 56-67.
International Written Opinion dated May 3, 2019 in International Application No. PCT/US16/61843. 10 pages.

* cited by examiner

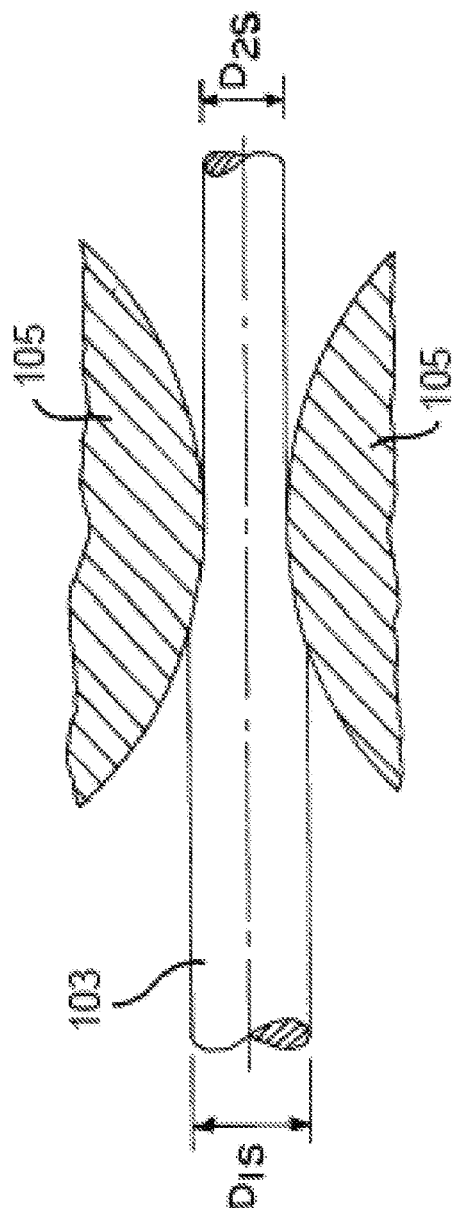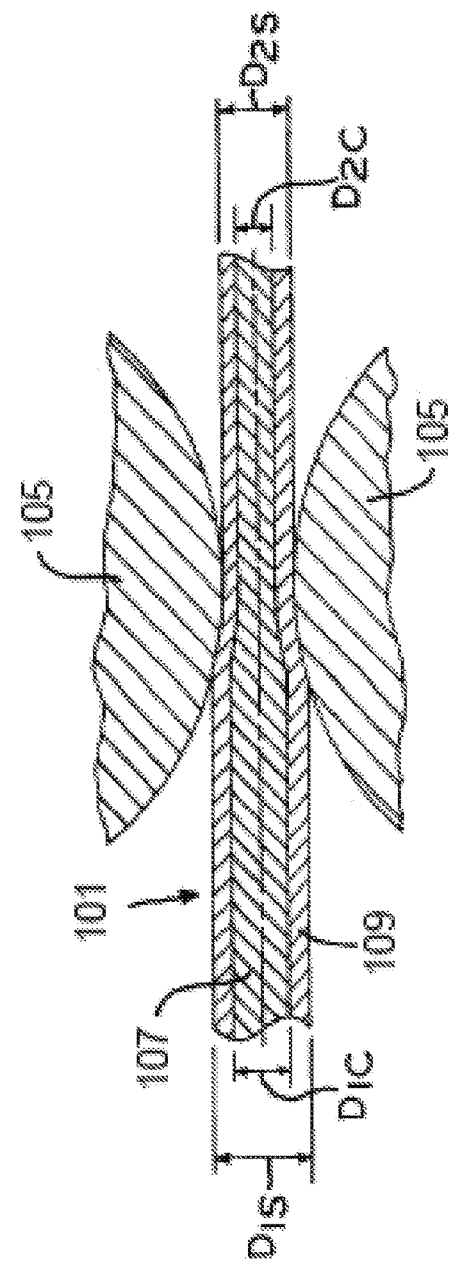

NI-FREE BETA TI ALLOYS WITH SHAPE MEMORY AND SUPER-ELASTIC PROPERTIES

RELATED APPLICATIONS

The present application is a national phase filing under 35 U.S.C. § 371 of International Application No. PCT/US2016/061843, titled "NI-FREE BETA TI ALLOYS WITH SHAPE MEMORY AND SUPER-ELASTIC PROPERTIES," filed on Nov. 14, 2016, the entire disclosure of which is expressly incorporated herein by reference.

BACKGROUND

1. Technical Field

The present disclosure is directed to shape-memory alloys and methods of making the same, and, in particular, to titanium-based shape-memory alloys lacking nickel as an alloy constituent.

2. Description of the Related Art

Specialized alloys have been developed for surgical implant applications. One such alloy, known as Nitinol (also commonly referred to as "NiTi"), is produced in bar and wire forms intended for use in surgical implants such as, for example, cardiac stents and pacing leads adapted to relay a cardiac pacing pulse from an implanted defibrillator or pacing device to the heart.

NiTi alloys have been widely used in medical applications due to their shape memory and super-elastic properties. This unique property allows materials or devices to recover relatively large deformation without permanent damage, which is desirable in some applications, such as minimally invasive surgery. NiTi alloys have been prominent in the medical device marketplace for high performance peripheral vascular products such as stents, guidewires, stylet wires, endovascular aneurysm repair devices, and embolic protection devices.

Some recipients of in vivo medical devices are sensitive (e.g., allergic) to nickel. For these recipients, an alloy is desired which lacks nickel while remaining suitable for its intended in vivo purpose, e.g., lumen-opening stent or a brain aneurysm-occluding textile.

Some prior efforts have focused on developing Ni-free superelastic alloys. During deformation of metastable beta Ti alloys, in order to accommodate the deformation strain, Stress-Induced Martensite Transformation (SIMT) occurs, where the beta phase (with a bcc crystal structure) transforms to martensite (with an orthorhombic crystal structure). If the stress induced martensite is not stable at the deformation temperature, reversal phase transformation will happen upon unloading, and the martensite transforms back to the beta phase. The strain associated with this phase transformation allows the material capable of recovering relatively large deformation without permanent damage, a property that is beneficial in some applications, such as medical devices.

SUMMARY

The present disclosure is directed to a group of substantially nickel-free beta-titanium alloys that have shape memory and super-elastic properties suitable for, e.g., medical device applications. In particular, the present disclosure provides a titanium-based group of alloys including 16-20 at. % of hafnium, zirconium or a mixture thereof, 8-17 at. % niobium, and 0.25-6 at. % tin. This alloy group exhibits recoverable strains of at least 3.5% after axial, bending or torsional deformation. In some instances, the alloys have a capability to recover of more than 5% deformation strain. Niobium and tin are provided in the alloy to control beta phase stability, which enhances the ability of the materials to exhibit shape memory or super-elastic properties at a desired application temperature (e.g., body temperature). Hafnium and/or zirconium may be interchangeably added to increase the radiopacity of the material, and also contribute to the superelasticity of the material.

In one form thereof, the present disclosure provides a substantially nickel-free beta-titanium alloy, comprising: between 16 at. % and 20 at. % hafnium, zirconium, or a combination thereof; between 8 at. % and 17 at. % niobium; between 0.25 at. % and 6 at. % tin; and balance titanium and impurities, wherein the alloy exhibits superelastic behavior with an isothermally recoverable strain of at least 3.5%, and wherein the alloy is formed into a shape set component.

In another form thereof, the present disclosure provides a substantially nickel-free beta-titanium material, comprising: between 16 at. % and 20 at. % hafnium, zirconium, or a combination thereof; between 8 at. % and 17 at. % niobium; between 0.25 at. % and 6 at. % tin; and balance titanium and impurities, wherein the material exhibits superelastic behavior with a isothermally recoverable strain of at least 3.5%., and wherein the material is a drawn construct.

In yet another form thereof, the present disclosure provides a method of making a substantially nickel-free beta-titanium alloy, the method comprising: providing between 16 at. % and 20 at. % hafnium, zirconium, or a combination thereof; providing between 8 at. % and 17 at. % niobium; providing between 0.25 at. % and 6 at. % tin; providing a balance of titanium and impurities; and shape setting the alloy.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 2A is a schematic view illustrating an exemplary process of forming monolithic wire using a lubricated drawing die;

FIG. 2B is a schematic view illustrating an exemplary process of forming composite wire using a lubricated drawing die;

Figures 1A, 1B:
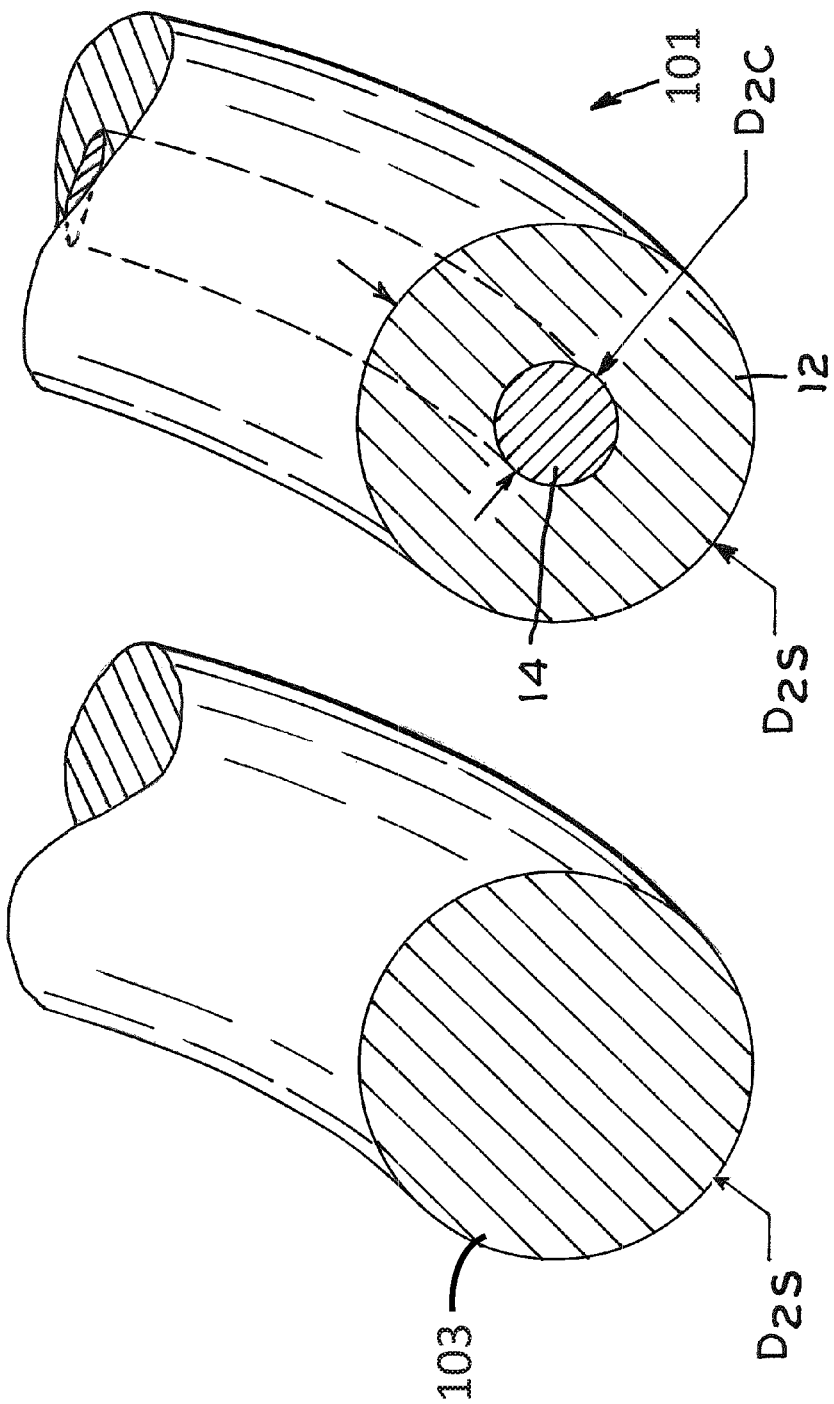
FIG. 1A is an perspective, cross-section view of a monolithic wire having diameter $D_{2S}$, in accordance with the present disclosure.
FIG. 1B is an perspective, cross-section view of a composite wire having overall diameter $D_{2S}$, in accordance with the present disclosure.

Corresponding reference characters indicate corresponding parts throughout the several views. Although the exemplification set out herein illustrates an embodiment of the invention, the embodiment disclosed below is not intended to be exhaustive or to be construed as limiting the scope of the invention to the precise form disclosed.

DETAILED DESCRIPTION

Introduction

The present disclosure provides a nickel-free superelastic alloy that exhibits improved recoverable strain properties. Such alloys contain nickel at a level at or below a 500 parts per million threshold for trace impurities. For example, wires and other structures may be made from Ti+(16-20)(Hf+Zr)+(8-17)Nb+(0.25-6)Sn (at. %). It has been found that structures made from this group of alloys, after receiving appropriate thermal conditioning as described below, exhibit recoverable strain properties competitive with nickel-based alloys and superior to other nickel-free alloys. In particular, the alloys of the present disclosure are suitable for applications in medical devices, e.g., for patients with a sensitivity to nickel.

Terminology

As used herein, "wire" or "wire product" encompasses continuous wire and wire products which may be continuously produced and wound onto a spool for later dispensation and use, such as wire having a round cross section and wire having a non-round cross section, including flat wire or ribbon. "Wire" or "wire product" also encompasses other wire-based products such as strands, cables, coil, and tubing, which may be produced at a particular length depending on a particular application. In some exemplary embodiments, a wire or wire product in accordance with the present disclosure may have a diameter up to 2.5 mm. In addition to wire and wire products, the principles of the present disclosure can be used to manufacture other material forms such as rod materials having a diameter greater than 2.5 mm up to 20 mm. Exemplary tubing structures may be in wire form or rod form, with inside diameters ranging from 0.5 mm to 4.0 mm, and wall thicknesses ranging from 0.100 mm to 1.00 mm. "Fine wire" refers to a wire having an outer diameter of less than 1 mm.

"Superelastic" material is material which is capable of undergoing strain exceeding 2% with negligible plastic deformation, such that the material is able to return to its original dimension after the deformation without permanent damage.

Figure 7:
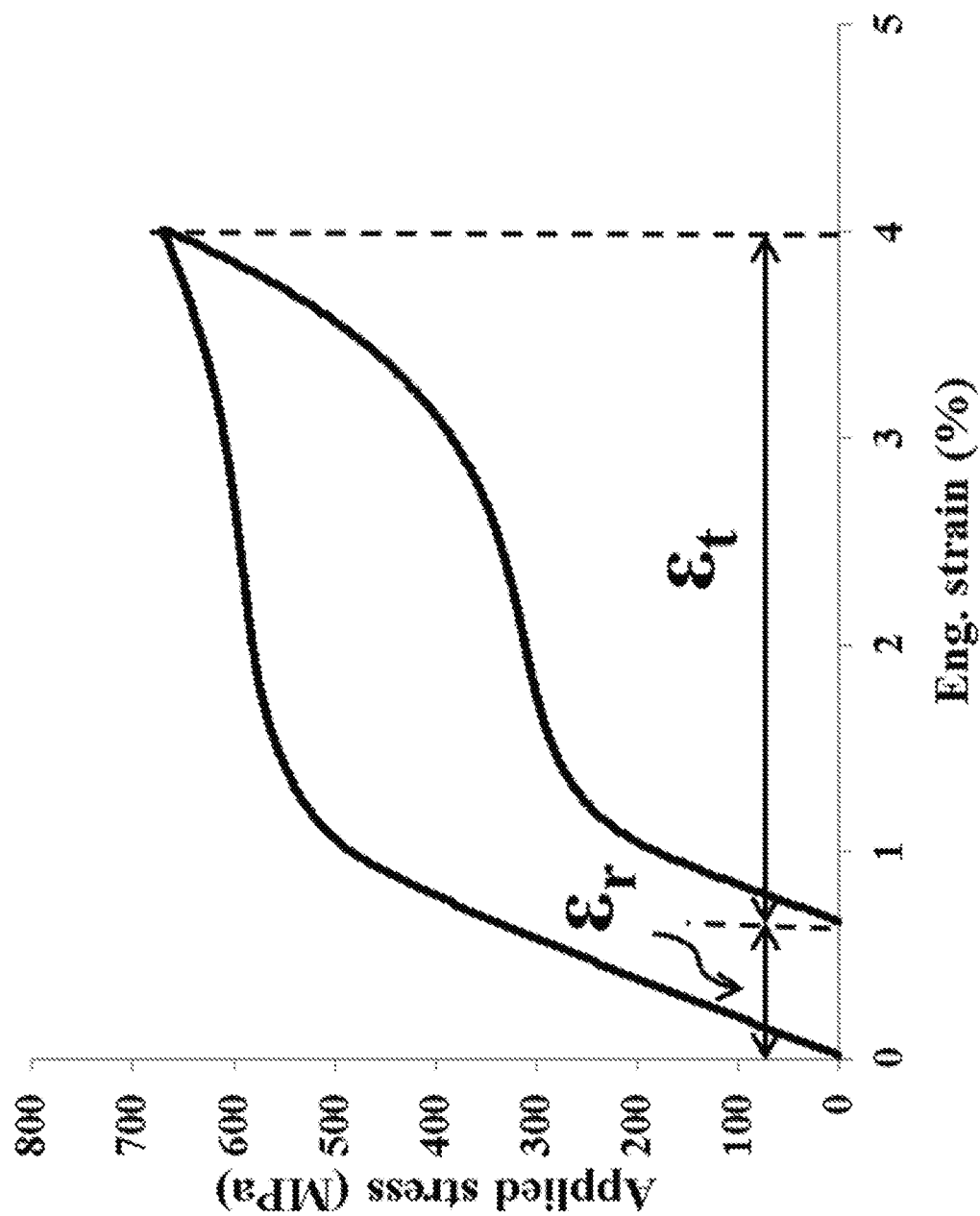
FIG. 7 shows a stress-strain curve in which a total deformation of 4% is imparted by application of stress.

"Recoverable strain" is defined as a total deformation strain during an application of force to a work piece, minus a residual strain, (FIG. 7) after unloading. The loading and unloading in generating the recoverable strain occurs above the active austenitic finish temperature (Af), or martensite reversion temperature (Mr), or when recovered above one of these said temperatures after lower temperature deformation. FIG. 7 shows a stress-strain curve in which a total deformation of 4% is imparted by application of stress (e.g., about 650 MPa as shown). After unloading, the work piece has a recoverable strain ($\varepsilon_r$, shown to be about 3.4%) and a non-recoverable strain ($\varepsilon_r$, shown to be about 0.6%), the sum of which is the total deformation of 4%.

"Isothermally recoverable strain" is recoverable strain observable in a substantially constant ambient temperature, i.e., without external heating or cooling of the work piece. The work piece may experience some internal heating or cooling from microstructural changes within an isothermal strain recovery. Ambient temperature may vary by a small amount during isothermal strain recovery, such as plus-or-minus 3° C. from the nominal temperature at the start of the stain recovery. Ambient temperature may be room temperature, i.e., 20-30° C., or body temperature, i.e., 36.4-37.2° C.

"DFT®" is a registered trademark of Fort Wayne Metals Research Products Corp. of Fort Wayne, Ind., and refers to a bimetal or poly-metal composite wire product including two or more concentric layers of metals or alloys, typically at least one outer layer disposed over a core filament formed by drawing a tube or multiple tube layers over a solid metallic wire core element.

As used herein, "fatigue strength" refers to the load level at which the material meets or exceeds a given number of load cycles to failure. Herein, the load level is given as alternating strain, as is standard for displacement or strain-controlled fatigue testing, whereby terms are in agreement with those given in ASTM E606, the entirety of which is incorporated herein by reference. For testing alternating strain via rotary beam fatigue testing, a wire sample is cut to a length of approximately about 118 mm (e.g., for a 0.33 mm diameter wire), then secured at its axial ends to rotatable jaws. The free portion of the wire between the jaws is bent to introduce a desired tensile strain at the "peak" or outermost portion of the bend. Directly opposite this peak of the bend, the wire experiences a compressive strain equal to the tensile strain, with the nominal value of both the tensile and compressive strains referred to herein as the "strain amplitude." The jaws are then rotated in concert (i.e., each jaw rotated with the same speed and in the same direction), such that the area of maximum tensile strain is rotated around the wire "peak" and transitioned to the area of maximum compressive strain with each 180-degree rotation of the jaws and wire. Rotary beam testing is further described in ASTM E2948-14, the entirety of which is hereby expressly incorporated herein by reference.

"Impurities," "incidental impurities" and "trace impurities" are material constituents present in a material at less than 500 parts per million or 0.05 wt. %. Alloys "free" of a certain constituent are alloys having such a constituent in amounts equal to or less the 500 parts per million impurities threshold. For example, "nickel free" alloys contain 500 parts per million or less of nickel. In some embodiments, such "nickel free" alloys may contain less than 250 parts per million, 150 parts per million or 100 parts per million of nickel, for example.

Titanium Alloyed with Niobium, Tin and Hafnium and/or Zirconium

Some applications, such as medical devices, benefit from materials which can be substantially deformed (e.g., by 4% or more) and be subsequently fully recovered without permanent damage or plastic deformation to the material. Such materials are commonly referred to as "superelastic" materials for their high capacity for elastic deformation with little or no plastic deformation. Traditionally, nickel-titanium materials have been good candidates for applications requiring superelastic materials. However, in some instances, such as medical devices used for patients with sensitivity or aversion to nickel, traditional NiTi-based alloys are not a suitable option. With recognition of these design constraints, materials made in accordance with the present disclosure provide substantially nickel-free beta-titanium materials which exhibit superelastic behavior suitable for use in, e.g., medical devices.

Nickel free superelastic alloys of the present disclosure include:

hafnium, zirconium, or a mixture thereof, in a total amount of 16-20 at. %;

niobium, in the amount of 8-17 at. %;

tin, in the amount of 0.25-6 at. %; and titanium and any impurities forming the balance of the alloy composition.

In the particular, an exemplary alloy in accordance with the present disclosure includes a concentration of hafnium, zirconium, or a combination of hafnium and zirconium as little as 16 at. %, 16.5 at. %, or 17 at. %, and as much as 19 at. %, 19.5 at. %, or 20 at. %, or any concentration in any range defined by any two of the foregoing values, such as 16 at. % to 20 at. %, 16.5 at. % to 19.5 at %, or 17 at. % to 19 at. %. For example, certain exemplary alloys have a hafnium/zirconium concentration of between 17 and 19 at. %. If the hafnium/zirconium concentration level falls below 16%, the resulting alloy will be martensitic at room and/or body temperature, rather than in the beta phase at these temperatures as is the case with the present alloy. Conversely, if the hafnium/zirconium concentration level rises above 20%, the resulting alloy will be stable in the beta phase (i.e., austenite) through the stress range of the material, such that stress-induced martensite transformation does not occur and the material is not capable of "shape memory" or "superelastic" behavior as described herein.

In addition, hafnium imparts radiopacity to the alloy, and the relative radiopacity behavior of the alloy can be adjusted by correspondingly adjusting the level of hafnium in the alloy as required or desired for a particular application. In some embodiments, zirconium may supplant some or all of the hafnium. Because zirconium can generally be obtained at a lower cost as compared to hafnium, the use of zirconium in place of hafnium can lower the overall cost of the present nickel-free alloy.

For purposes of the present disclosure, hafnium, zirconium, or a combination thereof may be referred to as "hafnium/zirconium" or "Hf/Zr," it being understood that this nomenclature includes constructions including entirely hafnium, entirely zirconium, or any combination of hafnium and zirconium to reach a specified concentration. However, where hafnium is used, either alone or in combination with zirconium, an alloy of the present disclosure includes at least 1 at. % hafnium and either zirconium or additional hafnium to reach the above-specified range of atomic percentages for hafnium or a hafnium/zirconium combination.

An exemplary alloy in accordance with the present disclosure includes a concentration of niobium as little as 8 at. %, 10 at. %, or 12 at. %, and as much as 14 at. %, 16 at. %, or 17 at. %, or may be any concentration in any range defined by any two of the foregoing values, such as 8 at. % to 17 at. %, 10 at. % to 16 at. %, or 12 at. % to 14 at. %, for example. For example, certain exemplary alloys have a niobium concentration of between 12.0 and 15.0 at. %. If the niobium concentration level falls below 8%, the resulting alloy will be martensitic at room and/or body temperature, similar to the result of Hf/Zr being below the enumerated range as described above. Conversely, if the niobium concentration level rises above 17%, the resulting alloy will not have the ability to generate stress-induced martensite and therefore will not exhibit superelastic behavior, also similar to the result of Hf/Zr being above the enumerated range.

An exemplary alloy in accordance with the present disclosure includes a concentration of tin as little as 0.25 at. %, 0.75 at. %, or 1.25 at. %, and as much as 5.0 at. %, 5.5 at. %, or 6.0 at. %, or may be any concentration in any range defined by any two of the foregoing values, such at 0.25 at. % to 6.0 at. %, 0.75 at. % to 5.5 at. %, or 1.25 at. % to 5.0 at. %, for example. For example, certain exemplary alloys have a tin concentration of between 2.0 and 5.0 at. %. If the tin concentration level falls below 0.25%, the resulting alloy does not exhibit superelastic behavior because stress-induced martensite will fail to revert or "recover" to austenite upon unloading. Conversely, if the tin concentration level rises above 6%, the material is rendered too stable in the beta phase to produce stress-induced martensite and the associated shape memory and superelastic behaviors.

An alloy in accordance with the present disclosure may be formed in bulk, such as by traditional casting methods. This bulk material is then formed into a suitable pre-form material (e.g., a rod, plate or hollow tube) by hot-working the bulk material into the desired pre-form size and shape. For purposes of the present disclosure, hot working is accomplished by heating the material to an elevated temperature above room temperature and performing desired shaping and forming operations while the material is maintained at the elevated temperature. The resulting pre-form material, such as an ingot, is then further processed into an intermediate form, such as a rod, wire or tube product by repetitive cold-forming and annealing cycles as further described below.

Table 1 below shows three particular exemplary alloys made in accordance with the present disclosure. As further described below, the alloys of Table 1 were produced and tested to test and verify material properties for selected alloys within the present Ti-(16-20)(Hf+Zr)-(8-17)Nb-(0.25-6)Sn group of alloys. Samples 1, 2 and 3 were arc melted, homogenized and extruded at 1000° C. to create an intermediate form, which was then drawn in to wire materials as described in detail below.

TABLE 1

| Exemplary Samples of Ti-(16-20)(Hf + Zr)-(8-17)Nb-(0.25-6)Sn Alloys | |
|---|---|
| Sample No. | Alloy Composition (at. %) |
| 1 | Ti—18Hf—14Nb—0.5Sn |
| 2 | Ti—18Hf—9Nb—5Sn |
| 3 | Ti—15Zr—11Nb—3Hf—3Sn |

Finished Constructs Including Ti—Hf/Zr—Nb—Sn

In one exemplary embodiment, Ti—Hf/Zr—Nb—Sn material made in accordance with the present disclosure may be formed into a medical-grade wire 101 or 103, as shown in FIGS. 1B and 1A respectively. Wires 101, 103 may have an outer wire diameter $D_{2S}$ of less than, e.g., 2.5 mm. Rod, tubes and other constructs may also be made, as described in detail below.

1. Drawing and Cold Work

Wires 101, 103 may be made by, for example, a schedule of drawing and annealing an intermediate material form (e.g., an ingot or rod) to create an initial coarse wire structure ready for final processing. Thereafter, wires 101 or 103 may be subjected to a cold work conditioning step (FIGS. 2A-2B) and one or more thermal processing steps such as shape setting, annealing and/or aging, in order to impart desired mechanical properties to the finished wire product as further described below.

In one exemplary embodiment shown in FIG. 2A, monolithic wire 103 made of the present nickel free beta titanium material, namely Ti–(16-20)(Hf+Zr)–(8-17)Nb–(0.25-6)Sn as expressed in atomic percentages, may be produced from a pre-form material into a wire of a desired diameter prior to final processing. That is, the pre-form material is drawn through one or more dies 105 (FIG. 2A) to reduce the outer diameter of the intermediate material slightly while also elongating the material, after which the material is annealed to relieve the internal stresses (i.e., retained cold work as discussed below) imparted to the material by the drawing process. This annealed material is then drawn through one or more new dies 105 with a smaller finish diameter to further reduce the diameter of the material, and to further elongate the material. Further annealing and drawing of the material is iteratively repeated until the material is formed into a drawn wire construct ready for final processing into wire 103.

To form composite wire 101 (FIG. 2B), such as DFT® brand composite wire, core 107 is inserted within shell 109 to form an intermediate construct, and an end of this intermediate construct is then tapered to facilitate placement of the end into a first drawing die 105 (FIG. 2B). The end protruding through the drawing die 105 is then gripped and pulled through the die 105 to reduce the diameter of the construct and bring the inner surface of shell 109 into firm physical contact with the outer surface of core 107. More particularly, the initial drawing process reduces the inner diameter of shell 109, such that shell 109 closes upon the outer diameter of core 107 such that the inner diameter of shell 109 will equal the outer diameter of core 107 whereby, when viewed in section, the inner core 107 will completely fill the central cavity of the outer shell 109 as shown in FIG. 2B. This process is iteratively repeated to further reduce the diameter of the material, which also further elongates the material similar to monolithic wire 103. Iterative annealing and drawing of the material is performed until the material is formed into a drawn wire construct ready for final processing into a drawn composite wire 101.

Drawn wire constructs are structurally distinguished from constructs formed by other methods (e.g., casting, machining, coating, etc.) by their characteristic smoothness and high reflectivity. In the case of a bimetallic composite wire construct having a core and a shell, the circularity of the cross-section and the concentricity of the shell and core are substantially finer in a drawn construct as compared to, e.g., a coated construct. In addition, the microstructure of a drawn construct may be structurally distinct from other constructs, for example by exhibiting an elongated grain structure (shown in FIG. 2D and further discussed below) or a fine-grain structure after thermal processing.

Exemplary composite wires 101 may be formed using a substantially nickel free, beta titanium alloy made in accordance with the present disclosure for either shell 109 or core 107. Other materials may be used in conjunction with the present Ti—Hf/Zr—Nb—Sn alloy as required or desired for a particular application. For example, the present Ti—Hf/Zr—Nb—Sn alloy may be used for shell 109 with a core 107 formed from platinum or tantalum, which provides a biocompatible and highly radiopaque wire structure.

Another example is the present Ti—Hf/Zr—Nb—Sn alloy used for core 107 with stainless steel or a superalloy used for shell 109, which may be desirable for, e.g., guide wire production. In particular, this construction provides a relatively stiff and pushable proximal guide wire section (owing to the higher stiffness of shell 109) and a relatively flexible and elastic distal guide wire section after taper grinding through shell 109 and into core 107 (owing to the lower stiffness of core 107). This construction may also be reversed, including stainless steel or a superalloy for core 107 and the present Ti—Hf/Zr—Nb—Sn alloy for shell 109, which provides for a relatively stiffer core 107 and more flexible shell 109. Thus a physician may gain proximal or distal stiffness depending on the therapy to be accomplished. Higher proximal stiffness can enable, e.g. better control over a distal tip with less greater torsional force transfer, while higher distal/tip stiffness can enable crossing of a tortuous chronic total occlusion (CTO), for example.

Yet another example is the use of the present Ti—Hf/Zr—Nb—Sn alloy used for shell 109 with core 107 made of a pure conductive metal, such as gold, platinum, tantalum, silver or niobium, for use as a pacing lead.

The step of drawing subjects wire 101 or 103 to cold work. For purposes of the present disclosure, cold-working methods effect material deformation at or near room temperature, e.g. 20-30° C. In the case of composite wire 101, drawing imparts cold work to the material of both shell 109 and core 107, with concomitant reduction in the cross-sectional area of both materials. The total cold work imparted to wire 101 or 103 during a drawing step can be characterized by the following formula (I):

$$cw = 1 - \left(\frac{D_2}{D_1}\right)^2 \times 100\% \qquad (I)$$

wherein "cw" is cold work defined by reduction of the original material area, "$D_2$" is the outer cross-sectional diameter of the wire (i.e., $D_{2S}$ for monolithic wire 103, and both $D_{2C}$ and $D_{2S}$ for composite wire 101) after the draw or draws, and "$D_1$" is the outer cross-sectional diameter of the wire (i.e., $D_{1S}$ for monolithic wire 103, and both $D_{1C}$ and $D_{1S}$ for composite wire 101) prior to the same draw or draws.

Referring to FIGS. 2A and 2B, the cold work step may be performed by the illustrated drawing process. As shown, wire 101 or 103 is drawn through a lubricated die 105 having an output diameter $D_{2S}$, which is less than diameter $D_{1S}$ of wire 101 or 103 prior to the drawing step. The outer diameter of wire 101 or 103 is accordingly reduced from pre-drawing diameter $D_{1S}$ to drawn diameter $D_{2S}$, thereby imparting cold work cw.

Alternatively, net cold work may be accumulated in wire 101 or 103 by other processes such as cold-swaging, rolling the wire (e.g., into a flat ribbon or into other shapes), extrusion, bending, flowforming, pilgering or cold-forging. Cold work may also be imparted by any combination of techniques including the techniques described here, for example, cold-swaging followed by drawing through a lubricated die finished by cold rolling into a ribbon or sheet form or other shaped wire forms. In one exemplary embodiment, the cold work step by which the diameter of wire 101 or 103 is reduced from $D_{1S}$ to $D_{2S}$ is performed in a single draw and, in another embodiment, the cold work step by which the diameter of wire 101 or 103 is reduced from $D_{1S}$ to $D_{2S}$ is performed in multiple draws which are performed sequentially without any annealing step therebetween.

For processes where the drawing process is repeated without an intervening anneal on composite wire 101, each subsequent drawing step further reduces the cross section of wire 101 proportionately, such that the ratio of the sectional area of shell 109 and core 107 to the overall sectional area of wire 101 is nominally preserved as the overall sectional area of wire 101 is reduced. Referring to FIG. 2B, the ratio of pre-drawing core outer diameter $D_{1C}$ to pre-drawings shell outer diameter $D_{1S}$ is the same as the corresponding ratio post-drawing. Stated another way, $D_{1C}/D_{1S}=D_{2C}/D_{2S}$. Further details regarding wire drawing are discussed in U.S. patent application Ser. No. 12/395,090, filed Feb. 27, 2009, entitled "Alternating Core Composite Wire", assigned to the assignee of the present invention, the entire disclosure of which is incorporated by reference herein.

2. Annealing

Thermal stress relieving, otherwise known in the art as annealing, at a nominal temperature not exceeding the melting point of the material or materials used in the construct, is used to improve the ductility of the construct between drawing steps, thereby allowing further plastic deformation by subsequent drawing steps. When calculating cold work cw using formula (I) above, it is assumed that no anneal has been performed subsequent to the process of imparting cold work to the material.

Heating wire 101 or 103 to a temperature sufficient to cause recrystallization of grains eliminates accumulated cold work. The cold work imparted by each iterative cold work process is relieved by fully annealing the material between draws, thereby enabling the next iterative cold working process. In full annealing, the cold-worked material is heated to a temperature sufficient to substantially fully relieve the internal stresses stored in the material, thereby relieving the stored cold work and "resetting" cold work to zero.

Figure 2C:
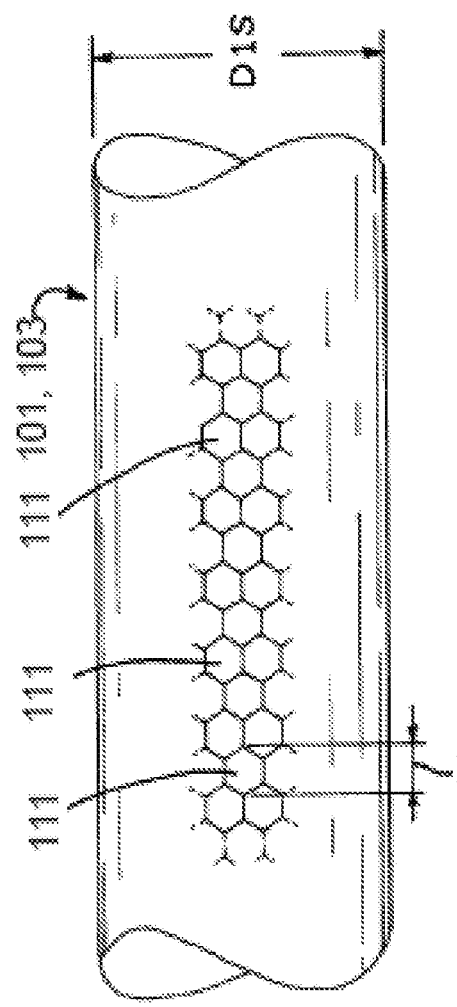
FIG. 2C is an elevation view of a wire in accordance with the present disclosure, before a final cold working process.
Figure 2D:
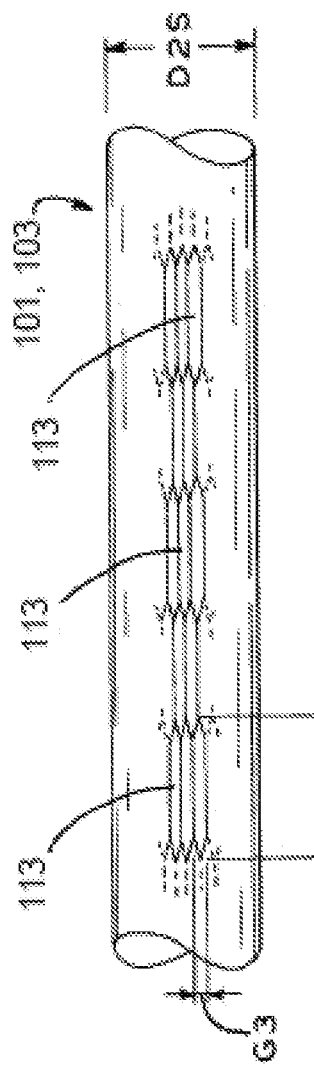
FIG. 2D is an elevation view of the wire of FIG. 2C, after the final cold working process.

On the other hand, wires 101 or 103 subject to drawing or other mechanical processing without a subsequent annealing process retain an amount of cold work. The amount of retained work depends upon the overall reduction in diameter from $D_{1S}$ to $D_{2S}$, and may be quantified on the basis of individual grain deformation within the material as a result of the cold work imparted. Referring to FIG. 2C, wire 103 is shown in a post-annealing state, with grains 111 shown substantially equiaxed, i.e., grains 111 define generally spheroid shapes in which a measurement of the overall length G1 of grain 111 is the same regardless of the direction of measurement. After drawing wire 101 or 103 (as described above), equiaxed grains 111 are converted into elongated grains 113 (FIG. 2D), such that grains 113 are longitudinal structures defining an elongated grain length G2 (i.e., the longest dimension across grain 113) and a grain width G3 (i.e., the shortest dimension across grain 113). The elongation of grains 113 results from the cold working process, with the longitudinal axis of grains 113 generally aligned with the direction of drawing, as illustrated in FIG. 2D.

The retained cold work of wire 101 or 103 after drawing can be expressed as the ratio of the elongated grain length G2 to the width G3, such that a larger ratio implies a grain which has been "stretched" farther and therefore implies a greater amount of retained cold work. By contrast, annealing wire 101 or 103 after an intermediate drawing process recrystallizes the material, converting elongated grains 113 back to equiaxed grains 111 and "resetting" the retained cold work ratio to 1:1 (i.e., no retained cold work).

For the present Ti—Hf/Zr—Nb—Sn materials, full annealing may be accomplished at a temperature about 600-750° C. for at least several seconds (e.g., 5-10 seconds) for thin wire (i.e., having a small cross-sectional area of between 0.000127 sq. mm and 0.5 sq. mm) to tens of minutes (e.g., 20-40 minutes) for thicker materials (i.e., having a larger cross-sectional area of between 1 sq. mm and 125 sq. mm). Alternatively, a full anneal can be accomplished with a higher temperature, such as between 750-1000° C., for a shorter time, such as between several milliseconds (e.g., 5-10 milliseconds) and less than 5 minutes, again depending on cross-sectional area of the material. Of course, a relatively higher temperature annealing process can utilize a relatively shorter time to achieve a full anneal, while a relatively lower temperature will typically utilize a relatively longer time to achieve a full anneal. In addition, annealing parameters can be expected to vary for varying wire diameters, with smaller diameters shortening the time of anneal for a given temperature. Whether a full anneal has been accomplished can be verified in a number of ways as well known in the art, such as microstructural examinations using scanning electron microscopy (SEM), mechanical testing for ductility, strength, elasticity, etc., and other methods.

Further discussion of cold working and annealing methods can be found in U.S. Pat. No. 8,840,735, filed Sep. 18, 2009 and entitled FATIGUE DAMAGE RESISTANT WIRE AND METHOD OF PRODUCTION THEREOF, the entire disclosure of which is hereby incorporated by reference.

3. Shape-Set Thermal Processing

After the initial iterative draw/anneal processing is completed, the resulting coarse wire material may then be finally processed into a final form, such as a fine wire suitable for integration into, e.g., a braided stent 100 (FIG. 8) having an overall device diameter $D_S$, a woven stent 110 (FIG. 9), or other medical device as further described below. Exemplary wire constructs are described in further detail below.

In particular, the coarse drawn material may be subject to a final cold work and subsequent "shape setting" process to form a wire or rod construct which exhibits superelastic behavior as described herein. "Shape setting" as used herein denotes a process in which a work piece (such as a wire) is constrained to a desired shape and thermally processed to retain the desired shape. For example, the work piece may be bent or otherwise formed into a desired shape, and held in that shape during subsequent thermal processing. In another example, the work piece may be constrained to its "natural" undeformed, pre-existing shape, which may include a straight shape. This "constraint" may not impart any stress to the material prior to thermal processing, but rather, may simply prevent the material from deforming away from the undeformed shape during subsequent thermal processing. With the work piece so constrained, the temperature of the work piece is increased in a thermal processing step until the work piece retains the desired shape, at which point the shape setting process is completed.

Shape setting may be performed on an-annealed material with no stored cold work with the scope of the present disclosure. However, shape setting materials with stored cold work produces larger recoverable strain capabilities for a given material geometry and constituency of the present Ti–(16-20)(Hf+Zr)–(8-17)Nb–(0.25-6)Sn alloy. In particular, using material with retained cold work in the present shape setting process raises the material's yield strength and mitigates or eliminates plastic deformation at a given level of strain, and produces certain crystal orientations favorable to robust strain recovery as compared to material without retained cold work. In an exemplary embodiment, final cold work processing is performed to impart a cold work as little as 50% or 75% and as much as 99% or 99.9%, or any cold work defined by any two of the foregoing values. In one exemplary embodiment, for example, a final cold work of about 90% is imparted to the work piece prior to shape setting.

In the shape setting process, the work piece is subjected to an ambient temperature (e.g., in an oven or other heater) between 500° C. and 1000° C. for a time period between 1 second and 1 hour or more. In particular, the temperature for this primary shape set be as little as 500° C., 550° C., or 600° C., and as much as 750° C., 800° C., or 1000° C., or may be any temperature in any range defined by any two of the foregoing values. The temperature at this stage may be held for as little as 1 second, 1 minute, or 15 minutes, and as much as 30 minutes, 45 minutes, or 1 hour or may be any period of time in any range defined by any two of the foregoing values.

As with annealing, time and temperature are inversely correlated in a shape setting process in accordance with the present disclosure. That is to say, shape setting at the upper range of acceptable temperatures will require a generally shorter time for a given work piece geometry (e.g., size and configuration), while the lower range of acceptable temperatures will required a relatively longer time.

Shape setting time is also dependent upon tin content of the alloy. Within the acceptable tin range of 0.25-6.0 at. % disclosed herein, a relatively lower tin concentration contributes to a relatively shorter shape set time, as compared to a relatively higher tin concentration requiring a longer shape set time. The shape set thermal conditions are sensitive to tin, because tin influences the beta phase stability of the alloy. Therefore the concentration of tin provided in the present Ti—Hf/Zr—Nb—Sn alloy may be varied in order to specifically influence or "tune" the shape setting time as required or desired for a particular application. For example, a shape setting process for pieces of individual wire may be subject to a lower-volume "batch" thermal treatment in which a number of discrete wires are simultaneously shape set. For such low-volume production, the longer shape setting process may be designed using relatively larger concentrations of tin, such as between 3 and 6 at. %. On the other hand, a continuous process may be desired for high-volume production of wire, in which case a quicker anneal may be facilitated by lower concentrations of tin, such as between 0.25 and 3 at. %.

For example, Sample 1 in Table 1 (above) has a low tin content at 0.5 at. % and the shape setting time of less than 10 seconds as shown in Table 2 (below) resulted in a superelastic, nickel-free alloy capable of recoverable strain in excess of 3.5% (with 4% measured as described further below). Conversely, Samples 2 and 3 were produced with higher levels of tin, at 5 at. % and 3 at. % respectively, and underwent shape setting times of 1 minute or more to achieve superelasticity.

Therefore, an alloy with a small cross-section (e.g., between $0.13 \times 10^{-6}$ and $176.7 \times 10^{-6}$ square inches) and a lower tin content (e.g., between 0.25 at. % and 3 at. %) may require thermal processing at this stage ranging from 1 second to 10 minutes at 500° C. to 1000° C. Conversely, an alloy with a larger diameter (e.g., between $176.7 \times 10^{-6}$ and $31.4 \times 10^{-3}$ square inches) and a higher tin content (e.g., between 3 at. % and 6 at. %) may require thermal processing at this stage ranging from 2 minutes to an hour or more at 500° C. to 1000° C.

4. Aging Thermal Processing

After the primary shape set thermal processing described above, the work piece may optionally be subject to a second thermal processing stage also known as "aging." In an exemplary embodiment, the work piece may be aged at a temperature as little as 150° C., 170° C., or 190° C., and as much as 210° C., 230° C., or 250° C., or any temperature in any range defined by any two of the foregoing values. The time of work piece exposure to this temperature may be as little as 1 second, 1 minute, or 15 minutes, and as much as 30 minutes, 45 minutes, or 1 hour, or may be any period of time in any range defined by any two of the foregoing values. In one particular exemplary embodiment, aging is completed at 200° C. for 10 minutes.

Figure 6:
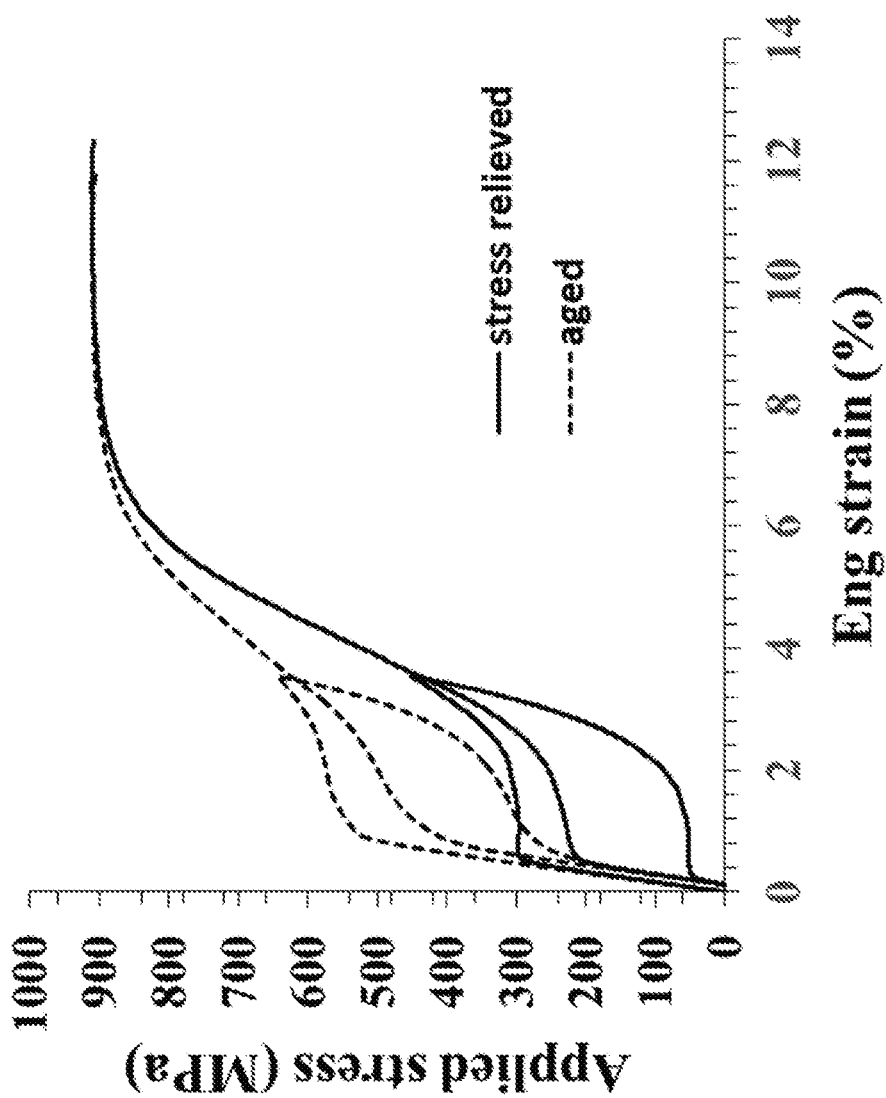
FIG. 6 is a pair of stress-strain curves for a pair of substantially nickel-free beta-titanium alloy according to the present disclosure, in which one curve is for an aged and sample and the other curve is for a stress-relieved sample.

Aging may be used to effect a portion of the shape set processing, and/or after primary shape setting, in order to "tune" material plateau stress levels to suit a particular application. More specifically, aging can be used to raise the plateau stress levels exhibited by a particular alloy as compared to a non-aged baseline. For example, FIG. 6 illustrates the effect of aging on an alloy made in accordance with the present disclosure. A stress-relieved sample which was not subject to aging was subjected to tensile testing to generate a baseline stress-strain curve, illustrated as a solid line in FIG. 6. As shown, the baseline plateau stress was about 300 MPa. Another sample of the same material was aged by heating at 200° C. for 10 minutes. After this aging treatment, tensile testing was again performed to generate a second stress-strain curve, illustrated as a dashed line in FIG. 6. As illustrated, the plateau stress of the aged material had been elevated to about 550 MPa, significant above the baseline.

This "tuning" potential provided by aging can help to provide a desired mechanical force profile for a particular material and/or medical device, in cooperation with overall mechanical design and other thermomechanical processing. Manipulation of plateau stress levels, either up or down compared to a non-aged baseline material, can be used to alter the force profile of the material. For example, plateau stress levels may be "tuned" to facilitate delivery of a medical device made of the present alloy, e.g., through a catheter. Alternatively or in addition to this delivery tuning, the plateau stress levels may also be tuned for a particular in vivo mechanical profile, e.g., the amount of chronic force to be exerted by the device in an anatomic vessel.

Thermal processing of material as described herein, including annealing, shape setting and aging, can be accomplished in any suitable fashion, including batch annealing of individual work pieces in an oven, fluidized bed furnace or forced convection furnace, and continuous annealing of spool-to-spool wire materials passing through a heated chamber, for example. Heating times and temperatures described herein are tailored for oven-based heating methods. Moreover, although heating methods all expose a work piece to an elevated ambient temperature for a specified time as described herein, it is also contemplated that heating of the work piece may be accomplished by any other suitable method. To the extent that such alternative heating modalities are employed, such alternative methods should be adjusted as necessary to produce an internal work piece temperature approximately equal to those reached by the ambient heating-based method described herein.

5. Exemplary Wire, Rod and Tube Structures

The previously discussed processing parameters can be used in various combinations to create materials suitable for different applications. Below are exemplary processing parameters for certain selected material sizes and geometries, it being understood that the exemplary conditions below may be substantially linearly extrapolated to determine processing parameters for material sizes and geometries between those listed below. For example, a wire with a diameter of 0.006 inches (i.e., between "ultra-fine" and "fine" materials described below) can be formed into a superelastic construct in accordance with the present disclosure by using processing parameters in a middle range between those listed below for wires with diameters of 0.003 and 0.009 inches respectively.

Figure 8:
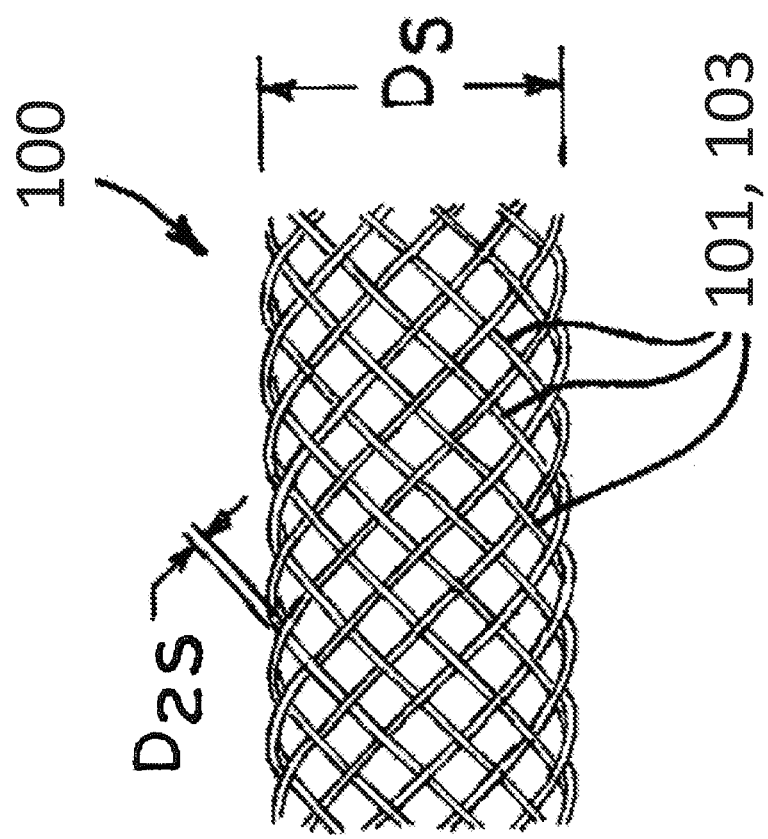
FIG. 8 is an elevation view illustrating the geometry of a braided stent having diameter $D_S$, the stent comprising wire elements formed into a mesh tubular scaffold, in accordance with the present disclosure.
Figure 9:
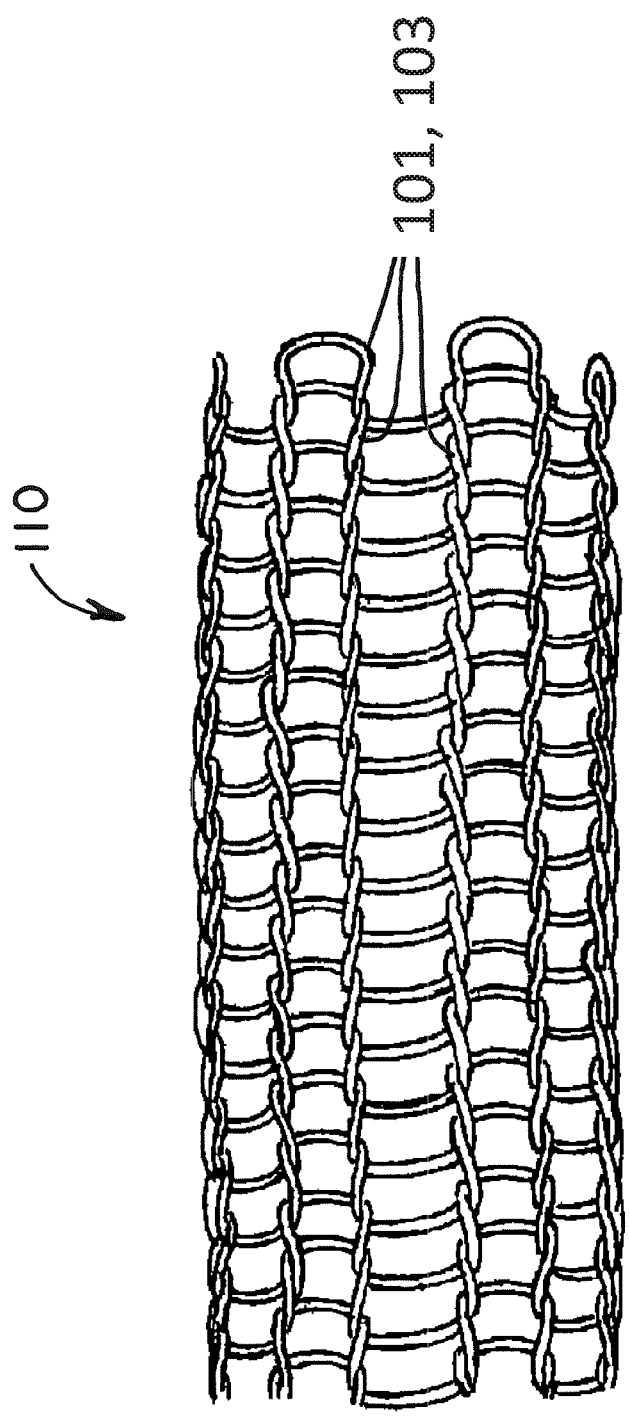
FIG. 9 is an elevation view illustrating the geometry of a woven stent comprising wire elements formed into a mesh tubular scaffold, in accordance with the present disclosure.

In one exemplary embodiment, the processing parameters can be adjusted for particular suitability for "ultra-fine" wire materials, e.g., wires with diameters between 0.0004 and 0.009 inches and/or cross-sectional areas between $0.13 \times 10^{-6}$ and $63.6 \times 10^{-6}$ square inches. In the medical device industry, ultra-fine materials are suitable for, e.g., textile applications such as stents (e.g., braided or woven stents 100, 110 as shown in FIGS. 8 and 9), aneurysm occlusion devices, embolic protection diverters, stents for vascular, renal and gastroenteral applications, heart septal wall closure scaffolds, bone spacer textiles for orthopedic implants, and blood filters.

For such ultra-fine materials, a high ratio of hafnium to zirconium (i.e., a relatively higher hafnium content for a given hafnium/zirconium concentration) may be desirable to ensure radiopacity of the resulting small construct. In an exemplary embodiment, such "high" hafnium to zirconium ratios are between 3:1 and 10:1, i.e., from three to 10 times more hafnium than zirconium for a given hafnium/zirconium concentration. Alternatively, some ultra-fine materials may have no zirconium and all hafnium to satisfy the above-described range of 8-17 at. % Hf/Zr in the present alloy. Given the temperature range of 500° C. to 1000° C. as discussed above, the shape set thermal processing time for such ultra-fine materials may be as little as 1 second, 5 seconds, or 30 seconds, and as much as 35 seconds, 50 seconds, or 1 minute, or may be any period of time in any range defined by any two of the foregoing values. For ultra-fine materials where material is wound around or otherwise placed over a mandrel, shape set thermal processing times may be longer to account for the heating of both the workpiece and the mandrel. In an exemplary embodiment, mandrel-based shape set thermal processing times for ultra-fine materials may be as little as 1 minute, 2 minutes, or 3 minutes and as much as 6 minutes, 8 minutes or 10 minutes, or may be any period of time in any range defined by any two of the foregoing values. As discussed above, the time and temperature of exemplary shape setting processes are inversely correlated.

In another exemplary embodiment, the processing parameters can be adjusted for particular suitability for "fine" wire materials, e.g., wires with diameters between 0.009 and 0.015 inches and/or cross-sectional areas between $63.6 \times 10^{-6}$ and $176.7 \times 10^{-6}$ square inches. In the medical device industry, fine materials are suitable for, e.g., guide wire applications including vascular, peripheral vascular and neurovascular guide wires, stylet wires, flexible laparoscopic and endoscopic components, wire-based stents, snare devices, bone-spacer textiles for orthopedic implants, and flexible heart valve components including a structural stent, frame or annulus.

For such fine materials, a moderate ratio of hafnium to zirconium is desirable to provide some radiopacity via the hafnium, while reducing cost by providing a substantial portion of the Hf/Zr concentration as zirconium. In an exemplary embodiment, such "moderate" hafnium to zirconium ratios are between 3:1 and 1:5, i.e., from three times more hafnium than zirconium to five times more zirconium than hafnium for a given hafnium/zirconium concentration. Given the temperature range of 500° C. to 1000° C. as discussed above, the shape set thermal processing time for such fine materials may be as little as 30 seconds, 45 seconds, or 1 minute, and as much as 4.25 minutes, 4.5 minutes, or 5 minutes, or may be any period of time in any range defined by any two of the foregoing values. As discussed above, the time and temperature of exemplary shape setting processes are inversely correlated.

In a further exemplary embodiment, the processing parameters can be adjusted for particular suitability for "medium to larger" wire materials, e.g., wires with diameters between 0.015 and 0.030 inches and/or cross-sectional areas between $176.7 \times 10^{-6}$ and $706.9 \times 10^{-6}$ square inches. In the medical device industry, medium and larger wire materials are suitable for, e.g., orthodontic applications such as archwires, guide wires including vascular, endovascular, laparoscopic, or esophageal guide wires, stylet wires, and flexible heart valve components including a structural stent, frame or annulus.

For such medium to larger materials, a low ratio of hafnium to zirconium is desirable to realize substantial cost reductions via the use of zirconium while also providing a desired level of radiopacity via a small amount of hafnium. In an exemplary embodiment, such "low" hafnium to zirconium ratios are between 1:5 and 1:8, i.e., from five to eight times more zirconium than hafnium for a given hafnium/zirconium concentration. Given the temperature range of 500° C. to 1000° C. as discussed above, the shape set thermal processing time for such medium to larger materials may be as little as 30 seconds, 1 minute, or 10 minutes, and as much as 20 minutes, 25 minutes, or 30 minutes, or may be any period of time in any range defined by any two of the foregoing values. As discussed above, the time and temperature of exemplary shape setting processes are inversely correlated.

In yet another exemplary embodiment, the processing parameters can be adjusted for particular suitability for large-diameter wire and "rod" materials, e.g., material stock with diameters between 0.080 and 0.200 inches and/or cross-sectional areas between $5.0 \times 10^{-3}$ and $31.4 \times 10^{-3}$ square inches. In the medical device industry, rod materials are suitable for, e.g., bone fixation devices, elastic bone nails for enhanced fusion, flexible bone plates, bone screws, and spinal rod applications for correction of spinal curvature.

For such rod materials, a very low ratio of hafnium to zirconium is desirable to maximize cost reductions via the use of zirconium. A very small amount of hafnium is sufficient to provide additional radiopacity, to the extent that such radiopacity is needed in a large rod-type structure. In an exemplary embodiment, such "very low" hafnium to zirconium ratios are between 1:8 and 1:17, i.e., from eight to 15 times more zirconium than hafnium for a given hafnium/ zirconium concentration. Alternatively, some rod materials may have no hafnium and all zirconium to satisfy the above-described range of 8-17 at. % Hf/Zr in the present alloy. Given the temperature range of 500° C. to 1000° C. as discussed above, the shape set thermal processing time for such rod materials may be as little as 5 minutes, 10 minutes, 20 minutes, and as much as 40 minutes, 50 minutes, or 60 minutes, or may be any period of time in any range defined by any two of the foregoing values. As discussed above, the time and temperature of exemplary shape setting processes are inversely correlated.

In addition to the wire and rod forms described above, tubing of similar dimensions may be produced using comparable processing parameters as those used for solid-cross-section structures. For example, tubing material sized to create a laser-cut vascular stent may be produced in the same manner as rod materials described above, it being understood that such tubular materials may receive thermal processing on a solid metal mandrel such that the overall time/temperature combinations are comparable to solid material. However, for such tubing applications designed for applications in which substantial amounts of material are removed from the tubing (e.g., laser-cut stents), a high ratio of hafnium to zirconium may be employed to ensure sufficient radiopacity despite substantial material removal.

After the shape setting process is completed, the resulting structure is transformed into a shape set material. Shape set material has several observable, structural characteristics which distinguish it from non-shape set materials. For example, shape set materials made in accordance with the present disclosure can be observed to transform between a beta phase (e.g., austenite) to martensite by application of stress, or temperature change, or both. Further, an unconstrained shape set material will hold its shape set geometry at temperatures above the austenite finish temperature. At temperatures below the austenite start temperature, the shape set material is capable of being deformed into, and retaining, a geometry different from the shape set geometry. This deformation has characteristics normally associated with plastic deformation, but as temperature is once again elevated above the austenite start temperature, the unconstrained shape set material will begin to revert back into the shape set geometry and will continue this reversion until the austenite finish temperature is reached.

Ti—Hf/Zr—Nb—Sn Material Properties

Exemplary monolithic Ti—Hf/Zr—Nb—Sn alloy wires in accordance with the present disclosure were produced, tested and characterized, particularly with regard to mechanical performance in a uniaxial tensile test. Such tests may be performed on an Instron Model 5565 test machine available from Instron of Norwood, Mass., USA. More specifically, destructive uniaxial tension testing of the wire materials was used to quantify the ultimate strength, yield strength, axial stiffness and ductility of candidate materials, using methods described in *Structure-Property Relationships in Conventional and Nanocrystalline NiTi Intermetallic Alloy Wire*, Journal of Materials Engineering and Performance 18, 582-587 (2009) by Jeremy E. Schaffer, the entire disclosure of which is hereby expressly incorporated herein by reference. These tests are run using servo-controlled Instron load frames in accordance with industry standards for the tension testing of metallic materials.

The group of Ti+(16-20)(Hf+Zr)+(8-17)Nb+(0.25-6)Sn alloys made in accordance with the present disclosure exhibit superelastic behavior, with recoverable strains (e.g., axial tensile strain recovery) in excess of 3.5% in drawn and shape set structures such as wires, rods and tubes. More particularly, the present group of alloys is capable of substantially complete strain recovery after a 4% strain, and greater than 5% recoverable strain after strains of 6-7%.

In addition to this ability for strain recovery, wires and materials made in accordance with the present disclosure may also possess mechanical and chemical characteristics which render the material particularly suitable for use in medical devices. For example, the present group of alloys is biocompatible within the meaning of ISO 10993, the entire disclosure of which is incorporated by reference herein. Additionally, the present group of alloys is substantially free of nickel, i.e., the amount of nickel present in the alloy is less than 0.05 wt. % and, in an exemplary embodiment, less than 0.01 wt. %.

Further, the present group of alloys may exhibit fatigue strength suitable for use in various medical device applications. In an exemplary embodiment, alloys made in accordance with the present disclosure exhibit a minimum fatigue strength to survive $10^6$ cycles at 0.5% alternating strain amplitude. Finally, the present group of alloys may have an ultimate tensile strength of at least 120 ksi (827 MPa), and in many cases, as high as 900 MPa, 950 MPa or greater.

Table 2 below shows thermal processing parameters for each of the alloy samples listed in Table 1 above, together with performance data from subsequent uniaxial tensile tests.

TABLE 2

Thermal Processing Parameters and Performance of Exemplary Alloys

| Sample No. | Alloy Composition (at. %) | Shape Set Temperature | Shape Set Time | Max. Recoverable Strain |
|---|---|---|---|---|
| 1 | Ti—18Hf—14Nb—0.5Sn | 650° C. | <1 second-6 seconds | >5% |
| 2 | Ti—18Hf—9Nb—5Sn | 650° C. | 1 minute | >5% |
| 3 | Ti—15Zr—11Nb-3Hf—3Sn | 600° C. | 2 minutes | >5% |

As noted above, each of the listed samples was arc melted, homogenized and extruded at 1000° C. After extrusion, each material was cold drawn by conventional wire drawing process to a diameter of 0.4 mm, creating a wire form ready for final thermal processing and tensile testing.

Figure 3:
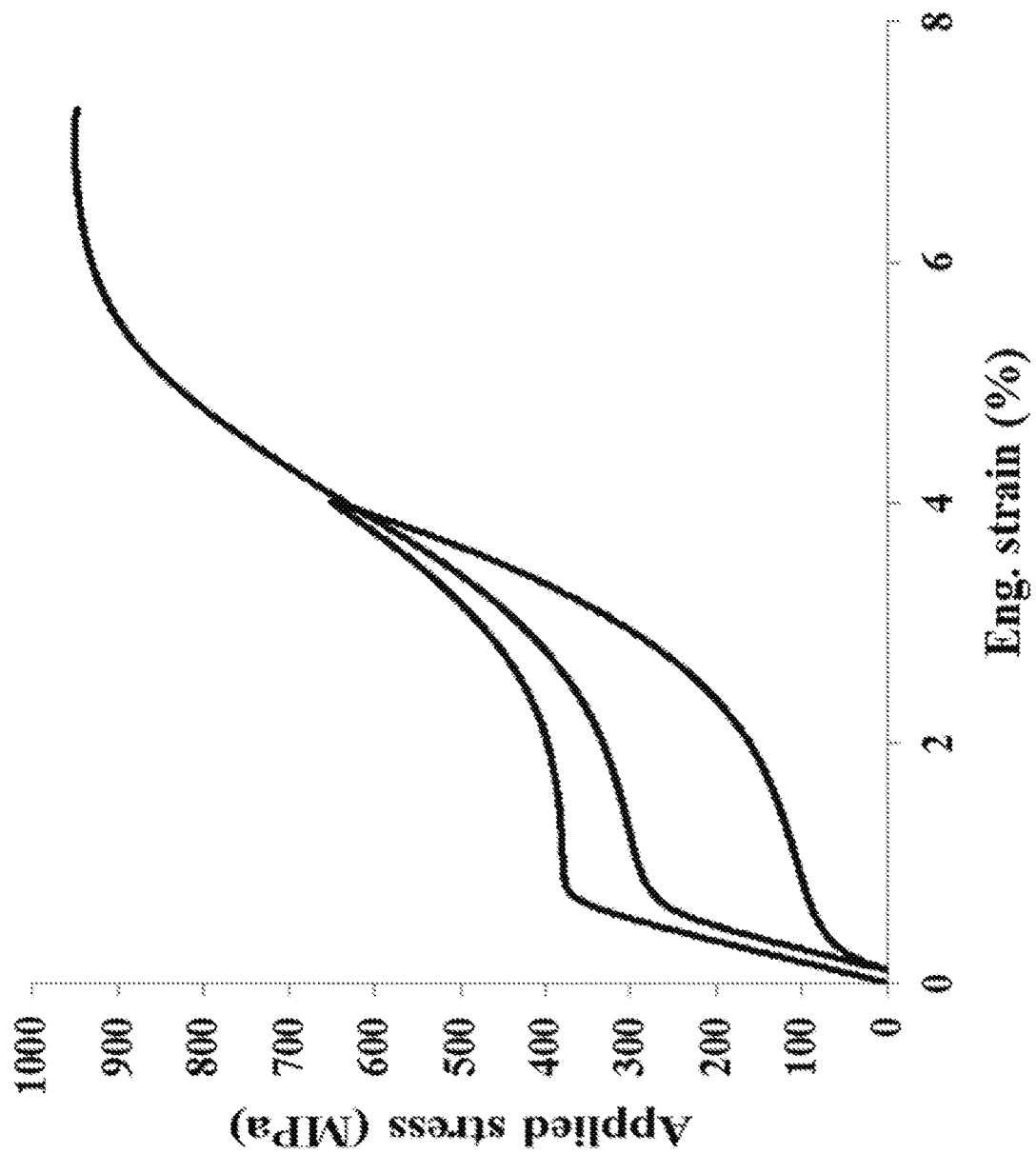
FIG. 3 is a pair of stress-strain curves for a substantially nickel-free beta-titanium alloy according to the present disclosure.

Sample 1 was heat treated at a temperature of 650° C. for a very short time (e.g. less than one second to about 6 seconds), as shown in Table 2. Tensile testing was then performed at room temperature, as stress and strain on the sample were measured and recorded at a substantially constant ambient temperature. FIG. 3 illustrates the stress-strain data collected during this testing. The sample was first loaded to achieve a strain of 4%, then unloaded to a zero stress. As shown in FIG. 3, Sample 1 was able to substantially completely recover this 4% deformation strain upon unloading at room temperature, with less than 0.1% non-recoverable strain.

Sample 1 was then loaded a second time, with the stress allowed to increase until failure (breakage) of the sample. Sample 1 exhibited an ultimate stress of about 950 MPa and achieved a strain in excess of 7% prior to failure.

Sample 1 was separately shown to be capable of exhibiting greater than 5% recoverable strain when subject to a 6% strain, as reflected in Table 2 above.

Therefore, Sample 1 was shown to exhibit superelastic properties suitable to provide nickel-free material for medical device applications. In particular, Sample 1 has a low tin content (i.e., 0.5 at. %) which enables rapid shape setting processes, as noted above, which facilitates high commercial throughput and maximized commercial productivity and value, particularly for fine and ultra-fine materials. Sample 1 is therefore an ideal candidate for wires in relatively large quantities for medical devices, such as textiles produced from thin filaments and guidewires or other straight devices, as discussed above.

Figure 4:
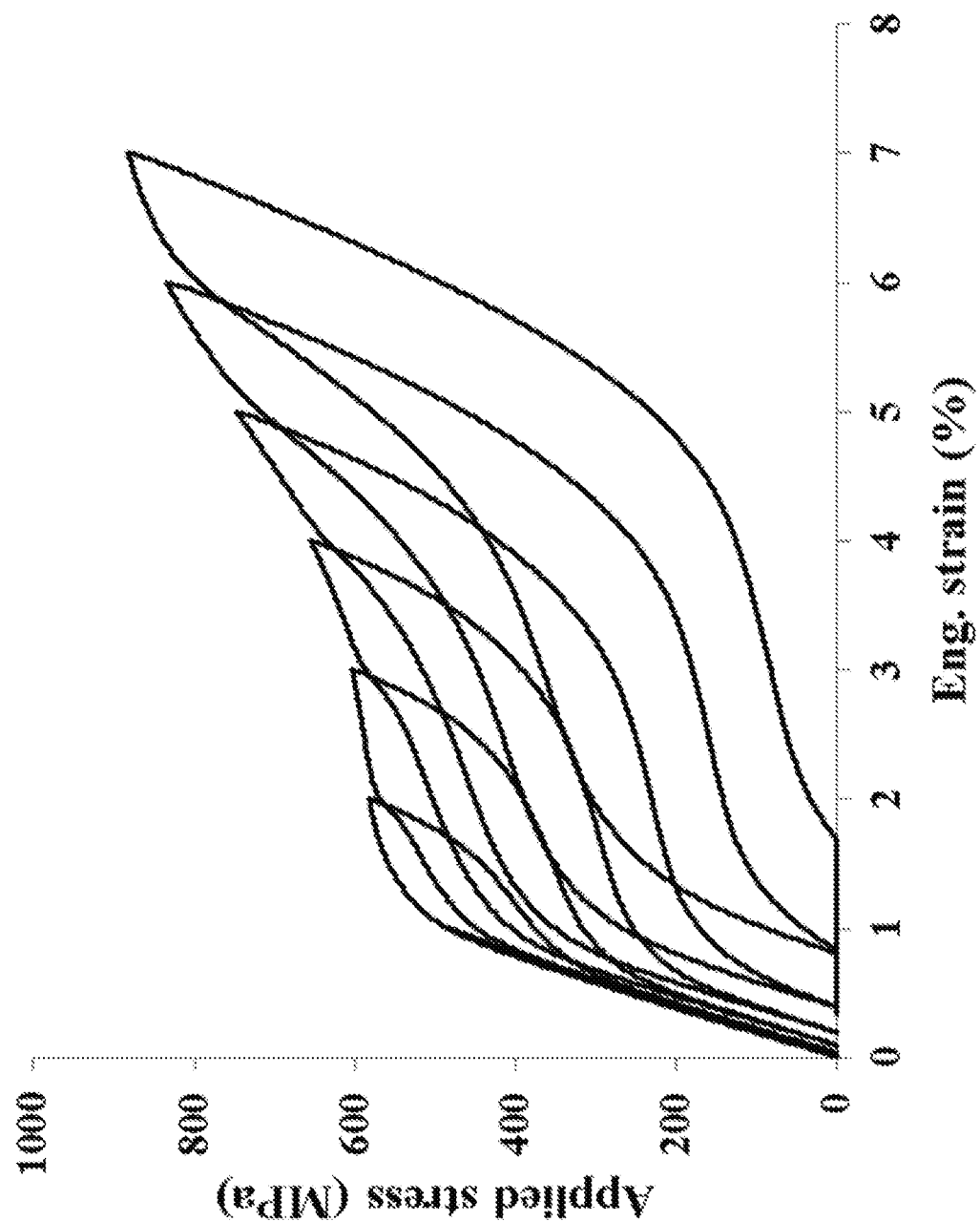
FIG. 4 is a series of stress-strain curves for another substantially nickel-free beta-titanium alloy according to the present disclosure.

Sample 2 was heat treated at a temperature of 650° C. for 1 minute, as shown in Table 2. Cyclic tensile testing was then performed at room temperature, as stress and strain on the sample were measured and recorded at a substantially constant ambient temperature. FIG. 4 illustrates the stress-strain data collected during this testing. The sample was first loaded to achieve a strain of 2%, then unloaded to a zero stress. Full recovery of the 2% strain was observed. A second loading cycle achieved a strain of 3%, again with a full strain recovery. A third loading cycle achieved a strain of 4%, and exhibited a substantially full recovery with residual strain less than 0.2%. A fourth loading cycle achieved a strain of 5%, and exhibited a substantially full recovery with residual strain less than 0.5%. A fifth loading cycle achieved a strain of 6%, and exhibited a strain recovery in excess of 5% with residual strain less than 1%. A sixth and final loading cycle achieved a strain of 7%, and exhibited a substantially full recovery with residual strain substantially less than 2%.

Therefore, Sample 2 was shown to exhibit superelastic properties suitable to provide nickel-free material for medical device applications. In particular, Sample 2 has a high tin content (i.e., 5 at. %) which enables a more prolonged shape setting process of one minute up to several minutes and is useful particularly for batch heat treatment production modalities, as noted above. This facilitates commercial applications in which a material is fixtured and held in shape by a secondary mass that must be heated for a prolonged period to achieve uniform heating, such as medium to larger and rod materials. Sample 2 is therefore an ideal candidate for Ni-free shape memory or superelastic rod and tubing applications currently served by shape set nitinol components, such as z-formed or stent-like structures, laser-cut stent components from tubular material, heart valve frames, mesh or woven support structures, spinal rods, etc. as discussed above.

Figure 5:
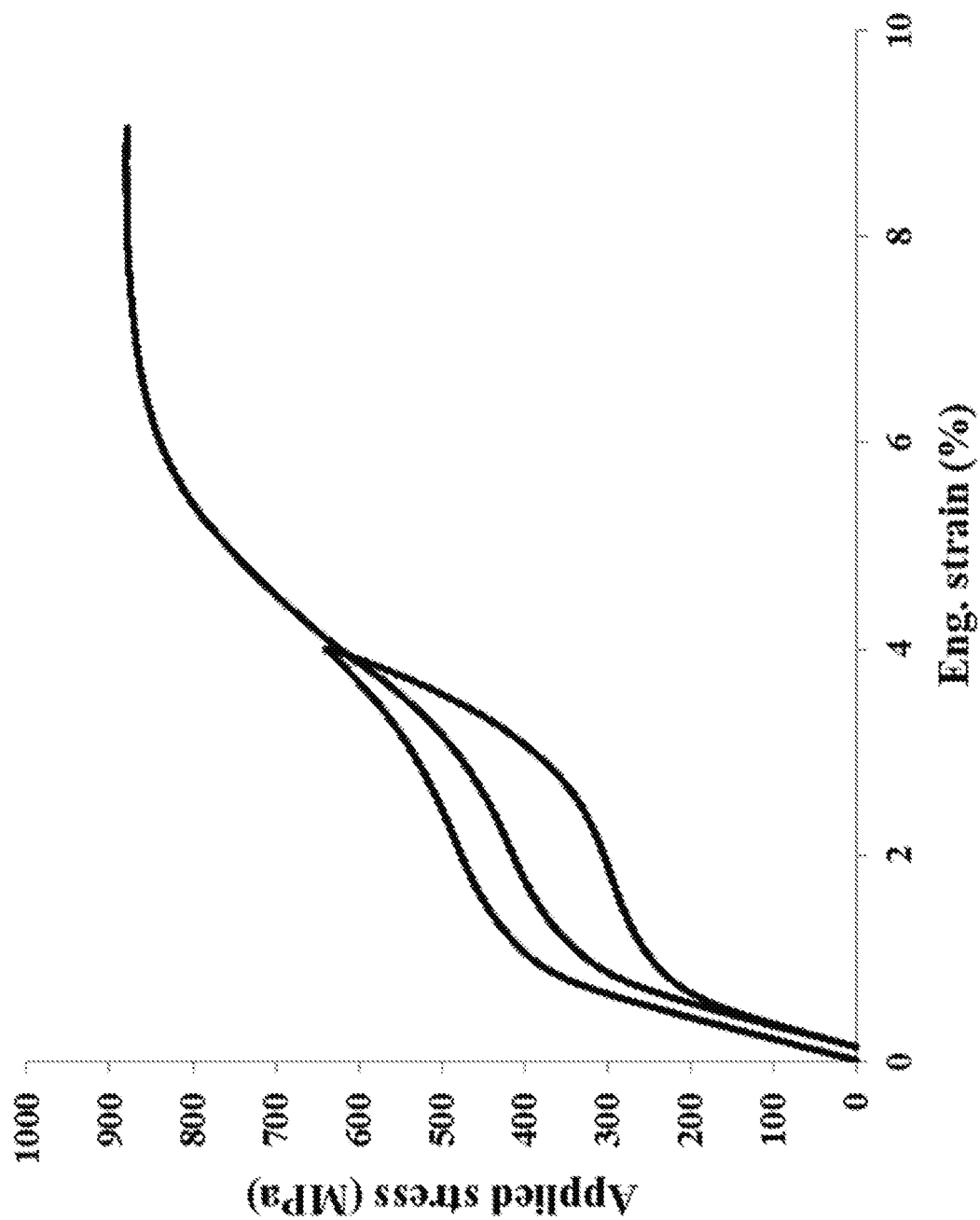
FIG. 5 is a pair of stress-strain curves for another substantially nickel-free beta-titanium alloy according to the present disclosure.

Sample 3 was heat treated at temperature of 600° C. for 2 minutes, as shown in Table 2 above. Cyclic tensile testing was then performed at room temperature, as stress and strain on the sample were measured and recorded at a substantially constant ambient temperature. FIG. 5 illustrates the stress-strain data collected during this testing. The sample was first loaded to achieve a strain of 4%, then unloaded to a zero stress. Substantially full recovery of the 4% strain was observed with residual strain less than 0.2%. The sample therefore showed a recoverable strain of about 3.8% after unloading from 4% deformation.

Sample 3 was then loaded a second time, with the stress allowed to increase until failure (breakage) of the sample. Sample 3 exhibited an ultimate stress in excess of 850 MPa and achieved a strain of about 9% prior to failure.

Sample 3 was separately shown to be capable of exhibiting greater than 5% recoverable strain when subject to a 6% strain, as reflected in Table 2 above.

Sample 3 displaces a substantial amount of hafnium with zirconium, using only 3 at. % hafnium and 15 at. % zirconium. As noted above, this material constituency reduces the radiopacity as compared to Samples 1 and 2, but also substantially reduces the cost of the material. As demonstrated by the tensile testing of sample 3, the material still exhibits superelastic properties with a total recoverable strain in excess of 3.5%. High-zirconium, low-hafnium materials such as Sample 3 are particularly suitable for applications that require a relatively large volume of material with limited need for radiopacity, such as orthodontic wires, spinal rods and orthopedic applications.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A substantially nickel-free beta-titanium alloy, comprising:
   between 16 at. % and 20 at. % hafnium, zirconium, or a combination thereof, wherein the alloy includes a minimum of 1 at. % hafnium;
   between 8 at. % and 17 at. % niobium;
   between 0.25 at. % and 6 at. % tin; and
   balance titanium and impurities,
   wherein the alloy exhibits superelastic behavior with an isothermally recoverable strain of at least 3.5%, and
   wherein the alloy is formed into a shape set component.

2. The alloy of claim 1, wherein the alloy exhibits superelastic behavior with an isothermally recoverable strain of at least 5%.

3. The alloy of claim 1, wherein the alloy includes zirconium, with a ratio of hafnium to zirconium between 3:1 and 1:17.

4. The alloy of claim 1, wherein the alloy includes between 16 at. % and 20 at. % hafnium and substantially no zirconium.

5. The alloy of claim 1, wherein the alloy exhibits the superelastic behavior at body temperature.

6. The alloy of claim 1, wherein the alloy is biocompatible.

7. The alloy of claim 1, wherein the shape set component is a drawn component.

8. The alloy of claim 7, wherein the drawn component is one of a wire, a tube and a rod.

9. The alloy of claim 7, wherein the drawn component is a wire having a cross-sectional area between $0.13 \times 10^{-6}$ and $63.6 \times 10^{-6}$ square inches and a ratio of hafnium to zirconium between 3:1 and 10:1.

10. The alloy of claim 7, wherein the drawn component is a wire having a cross-sectional area between $63.6 \times 10^{-6}$ and $176.7 \times 10^{-6}$ square inches and a ratio of hafnium to zirconium between 3:1 and 1:5.

11. The alloy of claim 7, wherein the drawn component is a wire having a cross-sectional area between $176.7 \times 10^{-6}$ and $706.9 \times 10^{-6}$ square inches and a ratio of hafnium to zirconium between 1:5 and 1:8.

12. The alloy of claim 7, wherein the drawn component is a rod having a cross-sectional area between $5.0 \times 10^{-3}$ and $31.4 \times 10^{-3}$ square inches and a ratio of hafnium to zirconium between 1:8 and 1:17.

13. The alloy of claim 7, wherein the drawn component is a composite wire comprising a shell having a central cavity and a core received within the shell.

14. The alloy of claim 1, wherein the alloy has retained cold work between 75% and 99%.

15. The alloy of claim 1, wherein the alloy comprises between 2.0 and 5.0 at. % tin.

16. The alloy of claim 1, wherein the alloy comprises less than 500 parts per million of nickel.

17. The alloy of claim 1, wherein the alloy comprises less than 0.01 wt. % nickel.

18. The alloy of claim 1, wherein the alloy exhibits fatigue strength such that the alloy survives 0.5% alternating strain for $10^6$ cycles.

19. The alloy of claim 1, wherein the alloy exhibits an ultimate tensile strength which reaches 120 ksi.

20. A substantially nickel-free beta-titanium material, comprising:
   between 16 at. % and 20 at. % hafnium, zirconium, or a combination thereof, wherein the alloy includes a minimum of 1% hafnium;
   between 8 at. % and 17 at. % niobium;
   between 0.25 at. % and 6 at. % tin; and
   balance titanium and impurities,
   wherein the material exhibits superelastic behavior with a isothermally recoverable strain of at least 3.5%, and
   wherein the material is a drawn construct.

21. The material of claim 20, wherein the material exhibits superelastic behavior with an isothermally recoverable strain of at least 5%.

22. The material of claim 20, wherein the material includes zirconium, with a ratio of hafnium to zirconium between 3:1 and 1:17.

23. The material of claim 20, wherein the material includes between 16 at. % and 20 at. % hafnium and substantially no zirconium.

24. The material of claim 20, wherein the drawn construct is one of a wire, a tube and a rod.

25. The material of claim 20, wherein the drawn construct has retained cold work between 75% and 99%.

26. The material of claim 20, wherein the material comprises between 2.0 and 5.0 at. % tin.

27. The material of claim 20, wherein the material comprises less than 500 parts per million of nickel.

28. The material of claim 20, wherein the drawn construct comprises less than 0.01 wt. % nickel.

29. The material of claim 20, wherein the drawn construct exhibits fatigue strength such that the material survives 0.5% alternating strain for $10^6$ cycles.

30. The material of claim 20, wherein the drawn construct exhibits an ultimate tensile strength which reaches 120 ksi.

31. The material of claim 20, wherein the alloy exhibits the superelastic behavior at body temperature.

32. The material of claim 20, wherein the alloy is biocompatible.

* * * * *